United States Patent
Anderson et al.

(10) Patent No.: US 8,977,333 B2
(45) Date of Patent: Mar. 10, 2015

(54) SHAPE-IMPARTING MECHANISMS FOR CATHETER ASSEMBLIES

(75) Inventors: Neil L. Anderson, Roseville (AU); Matthew Partlett, Allawah (AU)

(73) Assignee: Cathrx Ltd, Homebush Bay, NSW (AU)

( * ) Notice: Subject to any disclaimer, the term of this patent is extended or adjusted under 35 U.S.C. 154(b) by 1236 days.

(21) Appl. No.: 12/299,762

(22) PCT Filed: May 4, 2007

(86) PCT No.: PCT/AU2007/000600
§ 371 (c)(1),
(2), (4) Date: Jun. 3, 2009

(87) PCT Pub. No.: WO2007/128064
PCT Pub. Date: Nov. 15, 2007

(65) Prior Publication Data
US 2010/0030112 A1    Feb. 4, 2010

Related U.S. Application Data

(60) Provisional application No. 60/798,931, filed on May 8, 2006.

(51) Int. Cl.
*A61B 5/04* (2006.01)
*A61B 5/05* (2006.01)
*A61M 25/00* (2006.01)
(Continued)

(52) U.S. Cl.
CPC .......... *A61M 25/0041* (2013.01); *A61B 5/0422* (2013.01); *A61B 5/6856* (2013.01); *A61M 25/0152* (2013.01); *A61M 25/0009* (2013.01); *A61B 18/1492* (2013.01); *A61M 25/0068* (2013.01); *A61M 2025/0161* (2013.01); *B29C 53/083* (2013.01); *A61N 1/056* (2013.01)
USPC ........... 600/374; 600/547; 604/528; 604/530; 606/41; 606/46; 606/47

(58) Field of Classification Search
USPC .......... 600/549, 585, 547, 374; 604/528, 530; 606/41, 46, 47
See application file for complete search history.

(56) References Cited

U.S. PATENT DOCUMENTS 4,601,705 A * 7/1986 McCoy ...................... 604/95.05
5,016,808 A   5/1991 Heil et al.
(Continued)

FOREIGN PATENT DOCUMENTS

EP    0531946    3/1993
EP    1 048 314  11/2000
(Continued)

OTHER PUBLICATIONS

International Search Report mailed on Jul. 30, 2007 for PCT Application No. PCT/AU2007/000600, filed on May 4, 2007, six pages.
(Continued)

*Primary Examiner* — Sean Dougherty
(74) *Attorney, Agent, or Firm* — TraskBritt (57) ABSTRACT

A shape-imparting mechanism for a catheter that includes an elongate element dimensioned to fit within a lumen of an electrode sheath of a catheter. An insertion facilitating arrangement is carried at a distal end of the elongate element for facilitating insertion of the distal end of the elongate element into the lumen of the electrode sheath of the catheter.

10 Claims, 7 Drawing Sheets

(51) Int. Cl.
*A61B 5/042* (2006.01)
*A61B 5/00* (2006.01)
*A61M 25/01* (2006.01)
*A61B 18/14* (2006.01)
*B29C 53/08* (2006.01)
*A61N 1/05* (2006.01)

(56) References Cited

U.S. PATENT DOCUMENTS

| | | | |
|---|---|---|---|
| 5,112,309 A * | 5/1992 | Bertaud et al. | 604/171 |
| 5,282,845 A * | 2/1994 | Bush et al. | 607/128 |
| 5,327,905 A * | 7/1994 | Avitall | 600/585 |
| 5,497,786 A | 3/1996 | Urick | |
| 5,553,379 A * | 9/1996 | Westrum et al. | 29/450 |
| 5,601,572 A * | 2/1997 | Middleman et al. | 606/139 |
| 5,626,136 A | 5/1997 | Webster | |
| 5,632,746 A * | 5/1997 | Middleman et al. | 606/78 |
| 5,656,029 A * | 8/1997 | Imran et al. | 604/95.04 |
| 5,680,860 A * | 10/1997 | Imran | 600/374 |
| 5,683,445 A | 11/1997 | Swoyer | |
| 5,722,425 A | 3/1998 | Boström | |
| 5,728,148 A * | 3/1998 | Bostrom et al. | 607/116 |
| 5,807,339 A | 9/1998 | Boström et al. | |
| 5,997,526 A | 12/1999 | Giba et al. | |
| 6,270,496 B1 * | 8/2001 | Bowe et al. | 606/41 |
| 6,425,887 B1 * | 7/2002 | McGuckin et al. | 604/272 |
| 6,468,273 B1 * | 10/2002 | Leveen et al. | 606/41 |
| 6,575,967 B1 * | 6/2003 | Leveen et al. | 606/41 |
| 6,592,559 B1 * | 7/2003 | Pakter et al. | 604/272 |
| 6,663,588 B2 * | 12/2003 | DuBois et al. | 604/95.04 |
| 6,709,390 B1 * | 3/2004 | Marie Pop | 600/368 |
| 6,866,638 B2 * | 3/2005 | Dae et al. | 600/549 |
| 6,973,352 B1 | 12/2005 | Tsutsui | |
| 7,407,487 B2 * | 8/2008 | Dae et al. | 600/549 |
| 7,455,675 B2 * | 11/2008 | Schur et al. | 606/139 |
| 7,887,551 B2 * | 2/2011 | Bojarski et al. | 606/139 |
| 8,277,373 B2 * | 10/2012 | Maahs et al. | 600/107 |
| 8,641,697 B2 * | 2/2014 | Partlett et al. | 604/528 |
| 2001/0039413 A1 * | 11/2001 | Bowe | 604/532 |
| 2001/0044624 A1 * | 11/2001 | Seraj et al. | 606/41 |
| 2002/0072689 A1 * | 6/2002 | Klint | 600/585 |
| 2002/0087143 A1 | 7/2002 | Forsberg | |
| 2002/0169377 A1 | 11/2002 | Khairkhahan | |
| 2003/0032929 A1 * | 2/2003 | McGuckin, Jr. | 604/272 |
| 2003/0055402 A1 | 3/2003 | Zhou | |
| 2003/0199960 A1 | 10/2003 | Paskar | |
| 2004/0030259 A1 * | 2/2004 | Dae et al. | 600/549 |
| 2004/0054322 A1 * | 3/2004 | Vargas | 604/95.04 |
| 2004/0068242 A1 * | 4/2004 | McGuckin, Jr. | 604/272 |
| 2004/0220462 A1 * | 11/2004 | Schwartz | 600/374 |
| 2005/0159673 A1 * | 7/2005 | Dae et al. | 600/549 |
| 2005/0228290 A1 * | 10/2005 | Borovsky et al. | 600/466 |
| 2006/0009715 A1 * | 1/2006 | Khairkhahan et al. | 600/585 |
| 2006/0129101 A1 * | 6/2006 | McGuckin | 604/164.01 |
| 2006/0192465 A1 * | 8/2006 | Kornbluh et al. | 310/800 |
| 2006/0217755 A1 * | 9/2006 | Eversull et al. | 606/191 |
| 2008/0255539 A1 * | 10/2008 | Booth | 604/526 |
| 2008/0275388 A1 * | 11/2008 | Partlett et al. | 604/95.01 |
| 2009/0131865 A1 * | 5/2009 | Partlett et al. | 604/95.04 |

FOREIGN PATENT DOCUMENTS

| | | |
|---|---|---|
| JP | 09-173464 | 7/1997 |
| JP | 2002-513650 | 5/2002 |
| WO | 9833469 A1 | 8/1998 |
| WO | WO 99/22643 | 5/1999 |
| WO | 0071063 A1 | 11/2000 |
| WO | 0182810 A1 | 11/2001 |
| WO | WO-02/32497 A1 | 4/2002 |
| WO | WO-02/094334 A1 | 11/2002 |
| WO | 2004039273 A3 | 10/2004 |
| WO | WO-2006/012668 A1 | 2/2006 |

OTHER PUBLICATIONS

Written Opinion mailed on Jul. 30, 2007 for PCT Application No. PCT/AU2007/000600, filed on May 4, 2007, three pages.
U.S. Appl. No. 60/798,931, filed May 8, 2006, for Anderson et al.
Supplementary European Search Report completed Jun. 29, 2010, for European Patent Application No. 07 71 8847, eight pages.
Japanese Search Report for JP Application No. P2009-508051, dated May 24, 2011, 8 pages.
International Preliminary Report on Patentability for PCT/AU2007/000600, Dated Nov. 11, 2008.
Publication of European Search Report completed Mar. 21, 2014, for European Patent Application No. 13 199 220, seven pages.

* cited by examiner

SHAPE-IMPARTING MECHANISMS FOR CATHETER ASSEMBLIES

CROSS-REFERENCE TO RELATED APPLICATIONS

This application is a National Phase filing under 35 U.S.C. §371 of International Application No. PCT/AU2007/000600, filed May 4, 2007, designating the United States of America, and published in English, as PCT International Publication No. WO2007/128064A1 on Nov. 15, 2007, which claims the benefit of U.S. Provisional Patent Application No. 60/798,931, filed on May 8, 2006, the contents of which are incorporated herein by reference in its entirety.

FIELD

This invention relates, generally, to a steerable catheter and, more particularly, to a shape-imparting mechanism for a catheter and to a catheter including such a shape-imparting mechanism.

BACKGROUND

Electrophysiology catheters are medical devices that are used in measuring electrical signals within the heart, most often, in the diagnosis of various arrhythmias. These catheters are also used for treating arrhythmias via ablative techniques.

To access a region of the heart to be treated, the catheter is inserted through the femoral vein of the patient. The tip of the catheter is steered through the vascular system of the patient to the desired location. The catheter is introduced into the femoral vein of the patient using an introducer. In order to steer the catheter through the vascular system of the patient, it is desirable that the catheter have as small an outside diameter as possible. This can be achieved using a catheter manufactured according to the applicant's manufacturing techniques as described in its International Patent Application No. PCT/AU01/01339, dated Oct. 19, 2001 and entitled "An Electrical Lead." In International Patent Application No. PCT/AU01/01339, the wall of the electrical lead is formed by an inner tubular member about which electrical conductors are helically wound. An outer jacket is deposited over the electrical conductors. In so doing, the electrical conductors are embedded in the wall of the electrical lead leaving an unimpeded lumen.

It is often desired that the distal region of the catheter adopts a certain shape in order to effect ablation at a desired site in the patient's body. The applicants have filed International Patent Application No. PCT/AU2005/000216, dated Feb. 18, 2005 and entitled "A Steerable Catheter," which covers a steering shaft for use with its catheter that is received in the lumen of the catheter. A distal end of the steering shaft may be preformed in the desired shape to be imparted to the distal region of the electrode sheath of the catheter.

SUMMARY

According to a first aspect of the invention, there is provided a shape-imparting mechanism for a catheter, the shape-imparting mechanism including:
    an elongate element dimensioned to fit within a lumen of an electrode sheath of a catheter; and
    an insertion facilitating arrangement carried at a distal end of the elongate element for facilitating insertion of the distal end of the elongate element into the lumen of the electrode sheath of the catheter.

A tip of the elongate element may be rounded to aid insertion into the lumen of the electrode sheath of the catheter.

In an embodiment, a distal part of the elongate element may have an irregularly shaped configuration. The insertion facilitating arrangement may include a sleeve axially displaceable relative to the elongate element, the sleeve being displaceable between a first, extended position in which the sleeve collapses the irregularly shaped distal part of the elongate element into a substantially rectilinear configuration to facilitate insertion of the distal end of the elongate element into the lumen of the electrode sheath and a second, retracted position in which the distal part of the elongate element adopts the irregularly shaped configuration.

The elongate element may include a withdrawal inhibiting means at its distal end to inhibit withdrawal of the distal end into the sleeve. The withdrawal inhibiting means may be any device that enlarges a diameter of the distal end of the elongate element at least in one dimension. Thus, the withdrawal inhibiting means may be a deposit of an adhesive, a crimped region of the elongate element, an attachable collar, or the like.

At least the distal part of the elongate element may be of a shape memory material, which allows the distal part to adopt its irregularly shaped configuration when the sleeve is in its second, retracted position.

The elongate element may have a bend-enhancing portion arranged proximally of the irregularly shaped distal part, the sleeve, when in its second position, exposing the bend-enhancing portion to facilitate steering of the irregularly shaped distal part of the elongate element, in use.

In addition, or instead, the insertion facilitating arrangement may comprise a kink imparted to a distal part of the elongate element, proximally of the rounded tip of the elongate element.

When used in conjunction with the irregularly shaped configuration of the distal part of the elongate element, the kink may be arranged distally of the irregularly shaped configuration of the elongate element, the kink defining an angled distal portion, which is arranged at a predetermined, acute angle relative to an axis of that part of the elongate element arranged proximally of the kink.

According to a second aspect of the invention, there is provided a catheter assembly comprising:
    a handle having a proximal end and a distal end;
    a shape-imparting mechanism, as described above, extending from the distal end of the handle;
    an electrode sheath carried on the distal end of the handle with the shape-imparting mechanism being received within a lumen of the electrode sheath; and
    a control mechanism carried on the handle for effecting control of the insertion facilitating arrangement of the shape-imparting mechanism.

The control mechanism may comprise a slider arrangement that is axially slidably arranged on the handle to facilitate displacement of the sleeve from its first position to its second position and vice versa.

The electrode sheath may have a distal end preformed into a predetermined shape. The preformed distal end of the electrode sheath may have an irregular shape corresponding to, and imparted by, the irregularly shaped configuration of the distal part of the elongate element.

According to a third aspect of the invention, there is provided an electrode sheath for a catheter, the electrode sheath comprising:
    an elongate tubular element defining a lumen having a proximal end and a distal end; and a distal part of the tubular element being shaped into a predetermined configuration.

The distal part of the tubular element may be heat set into the predetermined configuration.

According to a fourth aspect of the invention, there is provided a method of fabricating an electrode sheath for a catheter, the method including:

providing an elongate tubular element having a malleable core, the core being removable;

forming a distal part of the tubular element into a predetermined, irregularly shaped configuration;

allowing the irregularly shaped distal part of the tubular element to set in that configuration; and removing the core.

The method may include heat setting the tubular element, with the core therein, in heating equipment for a predetermined period of time and, thereafter, removing the core.

Further, the method may include, after heat setting the tubular element, straightening the tubular element to facilitate removal of the core and, after removal of the core, allowing the tubular element to revert to its irregularly shaped, heat set configuration.

DETAILED DESCRIPTION OF EXEMPLARY EMBODIMENTS

Referring initially to FIGS. 1-4 of the drawings, a first embodiment of a shape-imparting mechanism for a catheter is illustrated and is designated generally by the reference numeral 10.

In this embodiment, the shape-imparting mechanism 10 includes an elongate element 12. The elongate element 12 is dimensioned to fit within a lumen of an electrode sheath 14 (FIG. 3) of a catheter.

The elongate element 12 is a tubular member 13 and has an actuator (not shown) arranged within the tubular member 13 as described in the applicant's co-pending International Patent Application No. PCT/AU2005/000216, referenced above. The actuator is fast with the tubular member 13 at a distal point 16 of the tubular member 13.

Figures 1, 2, 3, 4:
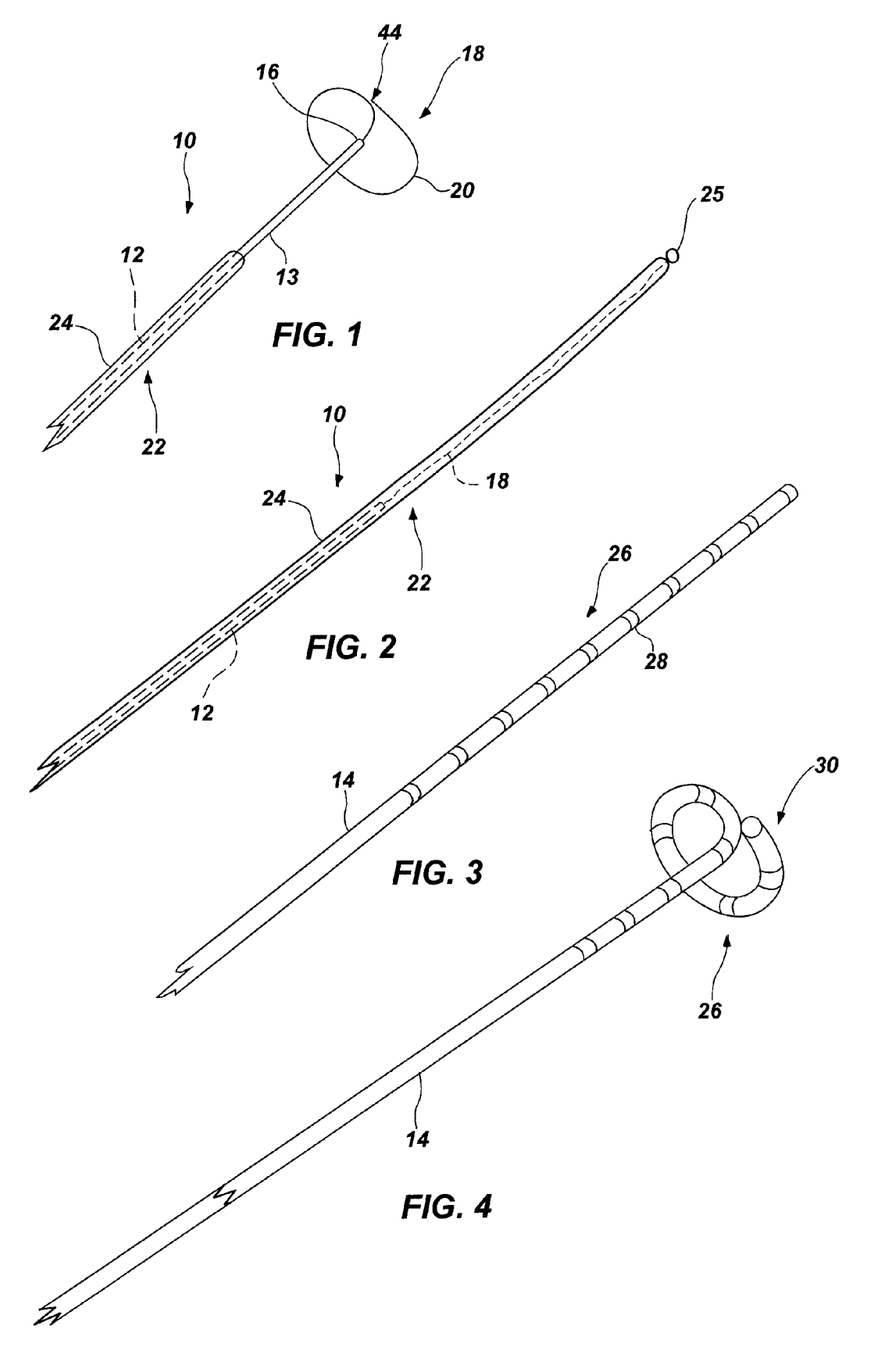
FIG. 1 shows a schematic, three-dimensional view of a distal part of a shape-imparting mechanism, in accordance with an embodiment of the invention, for a catheter with an insertion facilitating arrangement of the mechanism in a first, retracted position.
FIG. 2 shows a schematic, three-dimensional view of a distal part of the mechanism with the insertion facilitating arrangement in a second, extended position.
FIG. 3 shows a schematic, three-dimensional view of a distal part of an electrode sheath of a catheter with the shape-imparting mechanism of FIG. 1 received in a lumen of the electrode sheath with the insertion facilitating arrangement of the shape-imparting mechanism in its extended position.
FIG. 4 shows a schematic, three-dimensional view of a distal part of the electrode sheath of the catheter with the shape-imparting mechanism therein with the insertion facilitating arrangement in its retracted position.

A distal part 18 of the elongate element 12, distally of the point 16 has an irregularly shaped configuration 20, such as a loop-shape as shown in FIG. 1 of the drawings. It will, however, be appreciated that the distal part 18 of the elongate element 12 could have any other desired irregularly shaped configuration 20. The distal part 18 is, for example, implemented as an extension of the actuator received in the tubular member 13 as described in greater detail in PCT/AU2005/000216.

The shape-imparting mechanism 10 includes an insertion facilitating arrangement 22. In this embodiment, the insertion facilitating arrangement 22 is a sleeve 24 displaceably received on the elongate element 12. The sleeve 24 is axially displaceable on the elongate element 12 between a first, retracted position, shown in FIG. 1 of the drawings, in which the loop shape 20 of the distal part 18 of the elongate element 12 is exposed and a second, extended position, as shown in FIG. 2 of the drawings, in which the sleeve 24 overlies the distal part 18 of the elongate element 12 to collapse the elongate element 12 into a substantially rectilinear, or straight, configuration.

A distal end of the elongate element 12 carries a withdrawal inhibiting means in the form of an enlarged formation 25 (FIG. 2) such as a deposit of adhesive or a crimped formation to inhibit withdrawal of the extreme distal end of the elongate element 12 into the sleeve 24.

As described in applicant's co-pending Application No. PCT/AU2005/000216, referenced above, the steering mechanism described in that specification has a bend-enhancing portion arranged proximally of the distal point 16. When the sleeve 24 is in the second position, as shown in FIG. 2 of the drawings, the bend-enhancing region (not shown) of the tubular member 13 is exposed proximally of the sleeve 24 enabling the distal part 18 of the elongate element 12 to be steered through the patient's body to the desired site. When the distal part 18 of the elongate element 12 of the sleeve 24 is moved to its first position the bend-enhancing region of the tubular member 13 is exposed distally of the sleeve 24. This allows the irregularly shaped configuration 20 of the elongate element 12 to be steered to be maneuvered into position at the desired location at the site to be treated in the patient's body.

Thus, in use, for insertion of a catheter incorporating a shape-imparting mechanism 10 into the vasculature of the patient's body, the sleeve 24 is arranged in its second configuration, as shown in FIG. 2 of the drawings. The shape-imparting mechanism 10 is received within a lumen of the electrode sheath 14, as described above, so that, as shown in FIG. 3 of the drawings, a distal part 26 of the electrode sheath 14 carrying the electrodes 28 is, correspondingly, in a straight or rectilinear configuration. This facilitates steering of the distal part 26 of the electrode sheath 14 through the vasculature of the patient to the desired site in the patient's body.

A catheter incorporating the shape-imparting mechanism 10 of this embodiment is intended particularly for use in treating arrhythmias in the left atrium of the patient's heart. Thus, while the distal part 26 of the electrode sheath 14 is in its straight configuration, the electrode sheath 14 can be steered through the patient's heart into the right atrium, piercing the septum and into the left atrium. When in position in the left atrium, the sleeve 24 is withdrawn to its first position, as shown in FIG. 1 of the drawings, exposing the loop shape 20 of the distal part 18 of the elongate element 12. The distal part 18 of the elongate element 12 is of a shape memory alloy, such as Nitinol, so that, when the sleeve 24 is withdrawn to its first position, the distal part 18 adopts its preformed loop shape 20. When this occurs, a corresponding loop shape 30 (FIG. 4) is imparted to the distal part 26 of the electrode sheath 14 of the catheter.

Figures 5, 6:
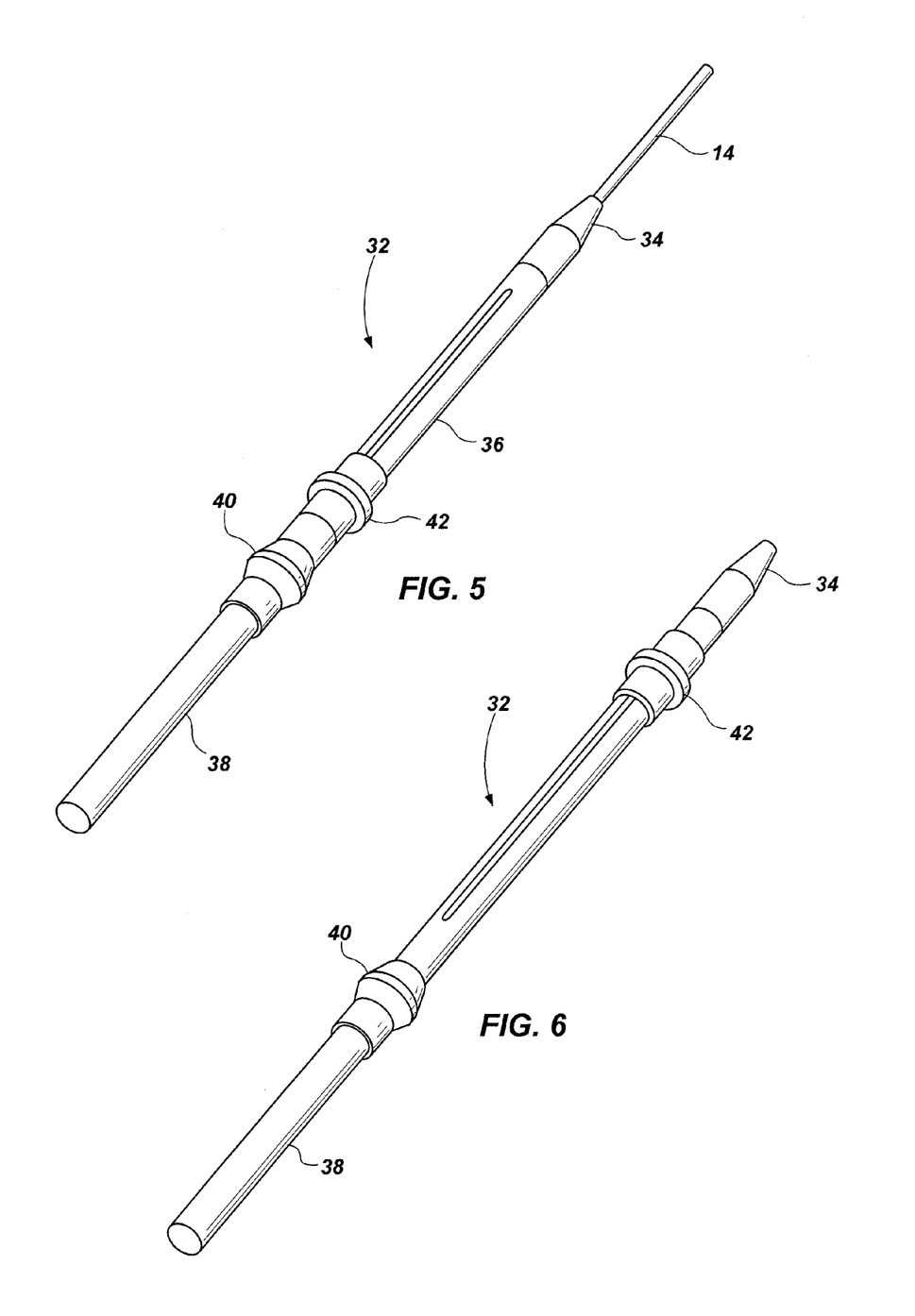
FIG. 5 shows a schematic, three-dimensional view of a catheter handle with a control mechanism for the shape-imparting mechanism in a first position.
FIG. 6 shows a schematic, three-dimensional view of the handle with the control mechanism in a second position.
Figure 7A:
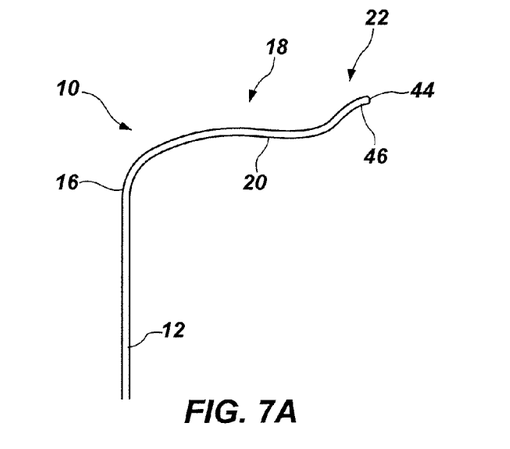
FIGS. 7A-7D show schematic, side views of distal parts of another embodiment of a shape-imparting mechanism for a catheter.
Figure 7B:
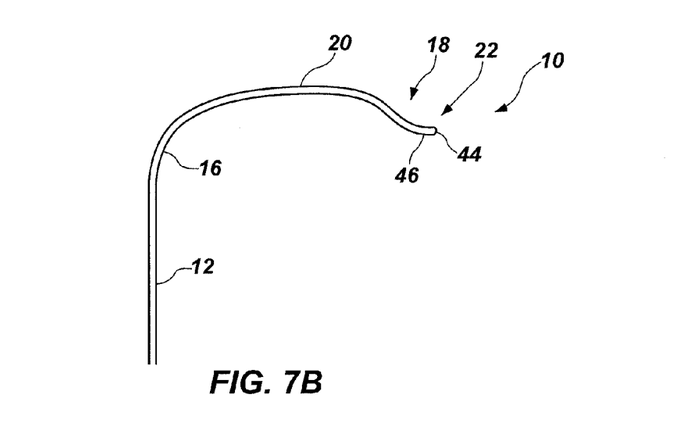
Figure 7C:
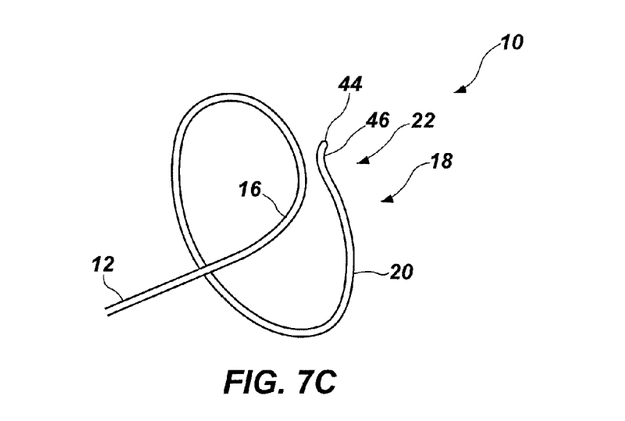
Figure 7D:
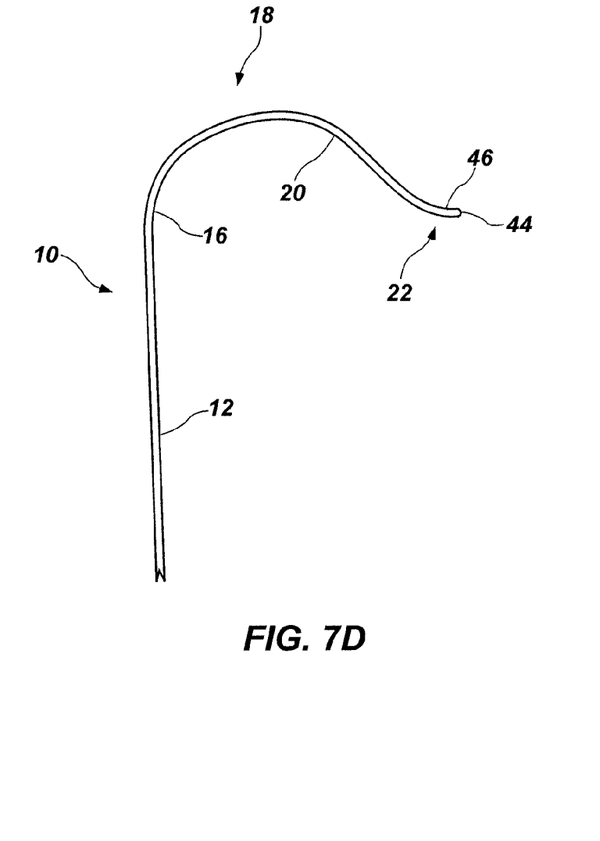

Referring now to FIGS. 5 and 6 of the drawings, a catheter assembly, in accordance with a further embodiment, is illustrated and is designated generally by the reference numeral 32. The catheter assembly 32 comprises the electrode sheath 14 mounted on a carrier 34 at a distal end of a handle 36 of the assembly 32. The handle 36 also carries the shape-imparting mechanism 10, which is not shown in FIGS. 5 and 6, as it is received within the lumen of the electrode sheath 14.

The handle 36 comprises an elongate body 38 with the carrier 34 mounted at a distal end of the body 38. A control mechanism in the form of a slide 40 is mounted on the handle 36 and is displaceable axially to control steering of the distal end 26 of the electrode sheath 14 via the shape-imparting mechanism 10, which is connected to the slide 40 within the body 38.

The assembly 32 includes a further control mechanism, also in the form of a slide 42, which is axially displaceable on the body 38 between a first position, as shown in FIG. 5 of the drawings and a second position as shown in FIG. 6 of the drawings. The sleeve 24 of the insertion facilitating arrangement 22 of the shape-imparting mechanism 10 is connected to the slide 42 so that, when the slide 42 is in the position shown in FIG. 5 of the drawings, the sleeve 24 is in its first position. Conversely, when the slide 42 is in its second position, as shown in FIG. 6 of the drawings, the sleeve 24 is, correspondingly, in its second position overlying the distal part 18 of the elongate element 12 of the shape-imparting mechanism 10.

Returning to FIG. 1 of the drawings, it is to be noted that a tip 44 of the distal part 18 of the shape-imparting mechanism 10 has a rounded configuration to facilitate insertion into the lumen of the electrode sheath 14 and to inhibit the formation of a discontinuity, which can snag on the wall of the lumen of the electrode sheath 14.

Referring now to FIGS. 7A-7D, 8 and 9 of the drawings, another embodiment of the shape-imparting mechanism 10 is illustrated. With reference to the previous drawings, like reference numerals refer to like parts, unless otherwise specified.

In this embodiment, the insertion facilitating arrangement 22 of the shape-imparting mechanism 10 comprises a kink 46 imparted to the distal part 18 of the elongate element 12 proximally of the rounded tip 44 of the elongate element 12. Further, the kink 46 is arranged distally of the irregularly shaped configuration 20 of the distal part 18 of the elongate element 12 to facilitate insertion of the irregularly shaped configuration 20 of the elongate element 12 into the lumen of the electrode sheath 14.

Figure 8:
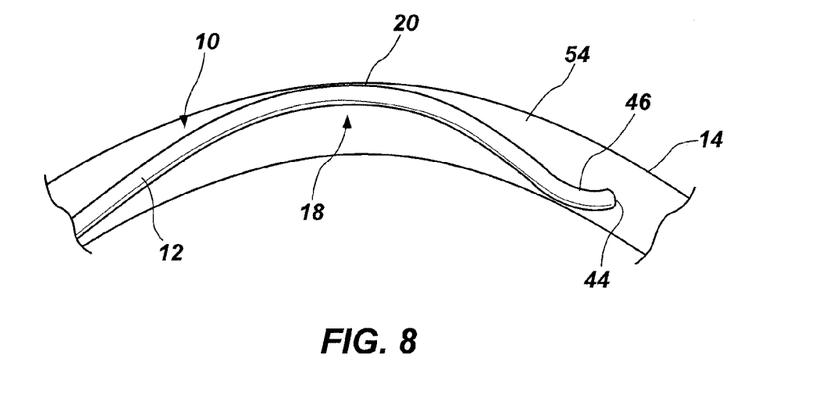
FIG. 8 shows a schematic, sectional side view of the mechanism of FIG. 7D being inserted into an electrode sheath of the catheter.
Figure 9:
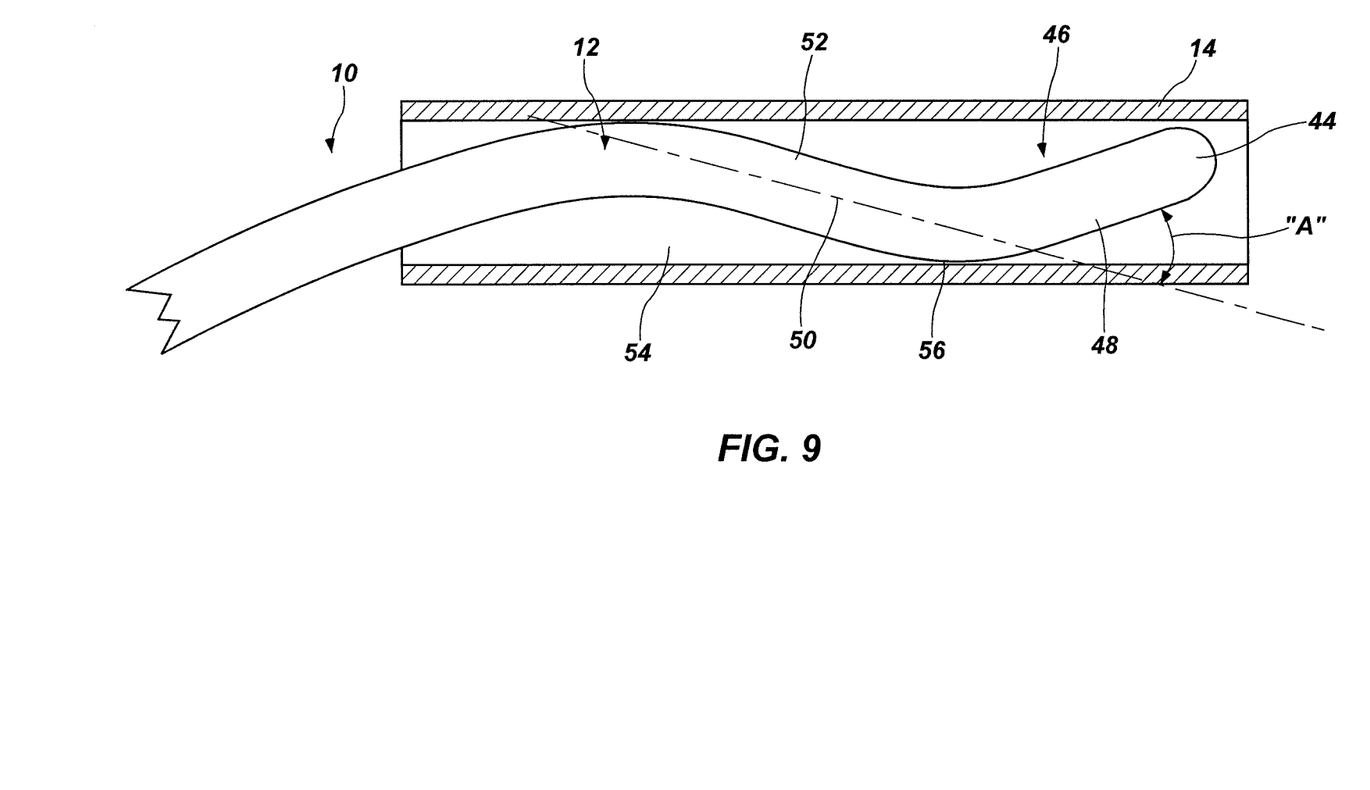
FIG. 9 shows a schematic, enlarged, sectional side view of the shape-imparting mechanism of FIG. 7D received in the electrode sheath of the catheter.
Figure 10:
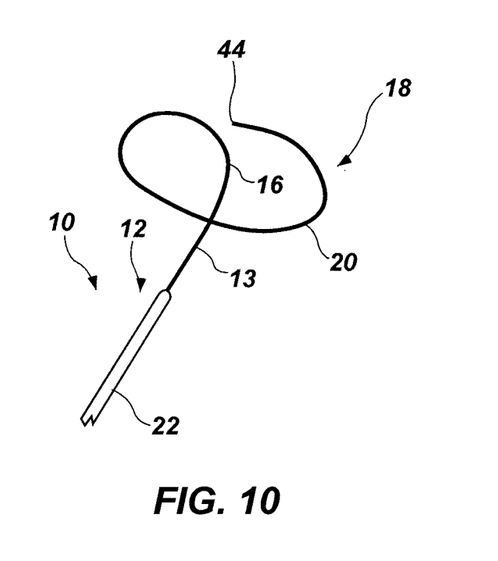
FIG. 10 shows a schematic, three-dimensional view of a distal part of a further embodiment of a shape-imparting mechanism for a catheter.
Figure 11:
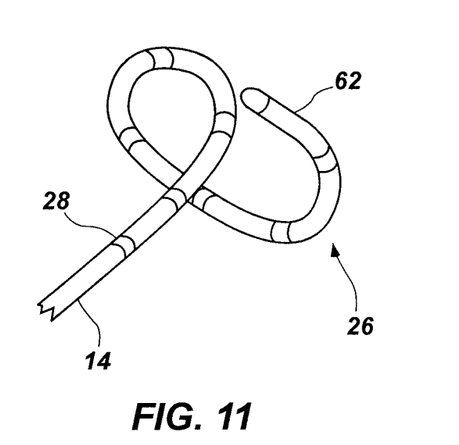
FIG. 11 shows a schematic, three-dimensional view of a distal part of an electrode sheath for use with the shape-imparting mechanism of FIG. 10.
Figure 12:
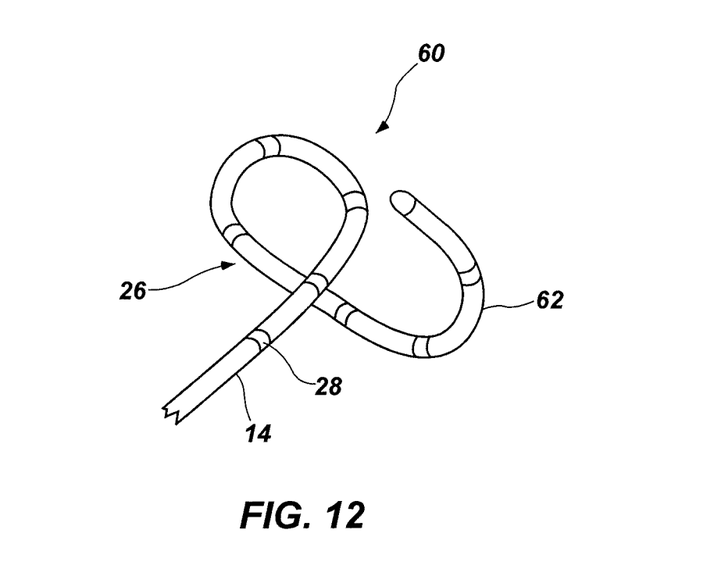
FIG. 12 shows the combination of the shape-imparting mechanism of FIG. 10 received in the electrode sheath of FIG. 11.

As illustrated more clearly in FIGS. 8 and 9 of the drawings, the kink 46 defines an angled distal portion 48, which is arranged at a predetermined, acute angle A (FIG. 9) relative to an axis 50 of a part 52 of the elongate element 12 arranged immediately proximally of the kink 46.

Typically, a lumen 54 (FIG. 9) of the electrode sheath 14 has an inner diameter of approximately 1 mm to 1.5 mm. The length of the kink 46 and the angle A are governed by the inner diameter of the lumen 54 of the electrode sheath 14. For example, the length of the kink 46 may be of the order of about 2 mm at an angle A of up to 45° to facilitate insertion of the irregularly shaped configuration 20 of the distal part 18 of the elongate element 12 into the lumen 54 of the electrode sheath 14.

FIGS. 7A-7D show variations of the irregularly shaped configurations 20, which could be imparted to the distal part 18 of the elongate element 12 of the shape-imparting mechanism 10. It will be understood that this is not an exhaustive illustration of the variations of irregularly shaped configurations 20 in which the distal part 18 could be configured. They are included for illustrative purposes only. It will, however, be noted that, in each case, the kink 46 is arranged distally of the irregularly shaped configuration 20 of the distal part 18 of the elongate element 12.

In this embodiment, in use, the elongate element 12 is inserted into the lumen 54 of the electrode sheath 14 by inserting the kink 46 into the lumen 54 of the electrode sheath 14. The rounded tip 44 and rounded transition 56 between the kink 14 and the part 52 of the distal part 18 of the elongate element 12 inhibits discontinuities and facilitates sliding movement of the distal part 18 of the elongate element 12 within the lumen 54 of the electrode sheath 14 of the catheter.

Referring now to FIGS. 10-15 of the drawings, another embodiment of a catheter assembly 60 is described. With reference to the previous drawings, like reference numerals refer to like parts, unless otherwise specified. In this embodiment, the catheter assembly 60 includes a shape-imparting element 10 such as that described above with reference to FIGS. 1-4 of the drawings. The assembly 60 also includes an electrode sheath 14.

The distal part 26 of the electrode sheath 14 is formed into an irregularly shaped configuration 62 corresponding to the irregularly shaped configuration 20 of the distal part 18 of the shape-imparting element 10. For example, as illustrated, the distal part 26 of the assembly 60 is formed into a loop shape 62.

The electrode sheath 14 is manufactured in accordance with the applicant's manufacturing technique as described in its International Patent Application No. PCT/AU01/01339, referenced above. In an initial step of the manufacturing process, an electrical lead is provided in which the lumen carries a core of a malleable material such as, for example, a copper core. To form the loop shape 62 at the distal part 26 of the electrode sheath 14, the distal part 26 is heat set into the required shape. This is achieved by forming the loop shape 62, with the copper core in the lumen of the electrode sheath 14 by plastically forming the copper core into the loop shape while the copper core is carried in the lumen of the electrode sheath 14. The electrode sheath 14 is then placed in an oven at a temperature of about 140° C. to 150° C. for approximately 5 minutes. This allows the distal part 26 of the electrode sheath 14 to set in the desired loop shape 62.

After heat treatment, the electrode sheath 14 is removed from the oven, is straightened out and the copper core is removed. When released from the straight shape, the plastics forming the lumen of the electrode sheath 14 re-forms into the loop shape 62.

Figures 13, 14, 15:
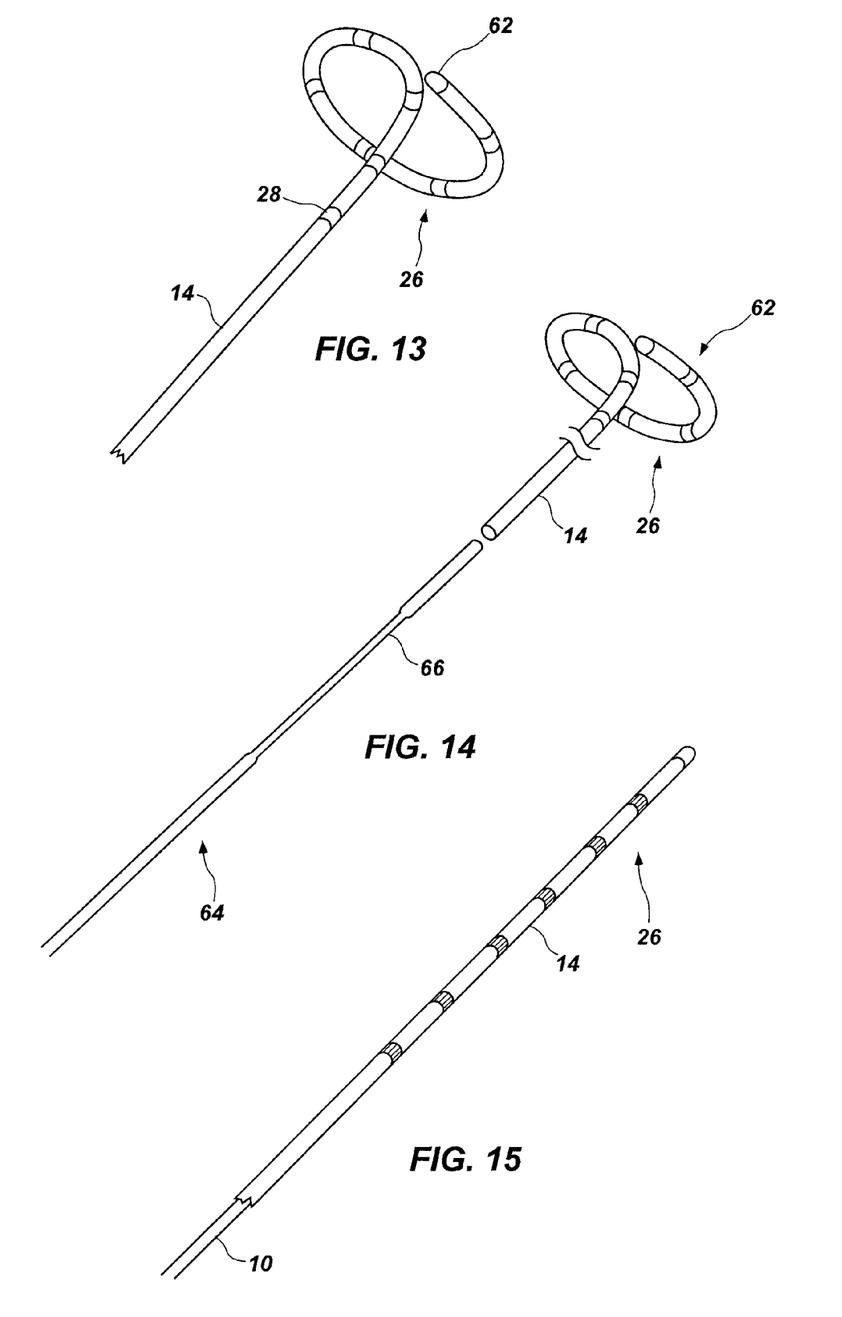
FIG. 13 shows a schematic, three-dimensional view of a distal part of an embodiment of an electrode sheath of a catheter.
FIG. 14 shows an initial stage in preparing the electrode sheath of FIG. 13 for insertion into a patient's body.
FIG. 15 shows the electrode sheath ready for insertion into the patient's body.

To use the assembly 60, the electrode sheath 14 is, initially, used with a straight stylet 64 (FIG. 14). The straight stylet 64 is of the type described in the applicant's co-pending International Patent Application No. PCT/AU2005/000216, referenced above. Thus, the stylet 64 has a bend-enhancing portion 66 at a distal region of the stylet 64.

The stylet 64 is inserted into the lumen of the electrode sheath 14 and is driven fully home so that the loop shape 62 is straightened out as shown in FIG. 15 of the drawings under the effect of the stylet 64. In other words, the distal part 26 of the electrode sheath 14 adopts a straight configuration.

In this configuration, the electrode sheath 14 is inserted into the vasculature of the patient's body and is steered to the desired site in the patient's body. At the desired site, the straight stylet 64 is removed from the lumen of the electrode sheath 14. Withdrawing the stylet 64 causes the loop shape 62 to re-form at the distal part 26 of the electrode sheath 14.

The shape-imparting element 10 is then inserted into the lumen of the electrode sheath 14. Prior to insertion, the sleeve 24 of the insertion facilitating arrangement 22 is moved to the position shown in FIG. 2 of the drawings so that the loop shape 20 at the distal part 18 of the shape-imparting mechanism 10 is straightened out.

When the tip of the shape-imparting mechanism 10 reaches the distal part 26 of the electrode sheath 14 and, prior to being inserted into the loop shape 62 of the electrode sheath 14, the sleeve 24 is withdrawn from the loop shape 20 of the shape-imparting mechanism 10. The distal part 18 of the shape-imparting mechanism 10 is, however, constrained in the lumen of the electrode sheath 14, which inhibits the loop shape re-forming.

The distal part 18 of the shape-imparting mechanism 10 is then driven fully home so that the distal part 18 of the shape-imparting mechanism 10 is coincident with the loop shape 62 of the electrode sheath 14. Because the distal part 18 of the shape-imparting mechanism 10 is similar to the loop shape 62 of the electrode sheath 14, when the distal part 18 is received within the loop shape 62 of the electrode sheath 14, the distal part 18 limits distortion of the distal part 62 of the electrode sheath 14 so that it maintains its desired preformed shape.

It will be appreciated that while the embodiment above has been described with reference to the distal parts 18 and 62 being loop-shaped, the distal parts 18 and 62 could be preformed into any desired shape necessary.

It is an advantage of the invention that a shape-imparting mechanism 10 is provided that facilitates insertion into the lumen of an electrode sheath 14 of a catheter. It is a further advantage of the invention that a catheter assembly 60 is provided that has a preformed distal shape 62 that is coincident with a preformed distal part 18 of a shape-imparting mechanism 10 received therein so that distortion of the distal part 62 of the electrode sheath 14 is limited when the shape-imparting mechanism 10 is received within the lumen of the electrode sheath 14.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A catheter assembly, comprising:
    an elongate element dimensioned to fit within a lumen of an electrode sheath of a catheter, the elongate element comprising:
        a distal end;
        a distal part having a curvilinearly shaped portion; and
        a bend-enhancing region located proximally of the curvilinearly shaped portion; and
    a sleeve being axially displaceable relative to the elongate element between an extended position in which the sleeve collapses the curvilinearly shaped portion of the elongate element into a substantially rectilinear configuration and exposes the bend-enhancing region proximally of the sleeve, and a retracted position in which the curvilinearly shaped portion of the elongate element adopts a curvilinear shape and the sleeve exposes the bend-enhancing region distally of the sleeve to facilitate steering of the curvilinearly shaped portion of the elongate element; and
    an electrode sheath receiving the elongate element within a lumen of the electrode sheath, the electrode sheath covering the distal end of the elongate element in the retracted position.

2. The catheter assembly of claim 1, wherein a tip of the distal end of the elongate element is rounded to aid insertion into the lumen of the electrode sheath of the catheter.

3. The catheter assembly of claim 2, wherein the elongate element includes a withdrawal inhibiting means at the distal end to inhibit withdrawal of the distal end into the sleeve.

4. The catheter assembly of claim 1, wherein at least the distal part of the elongate element comprises a shape memory material, which allows the distal part to adopt the curvilinear shape when the sleeve is in the retracted position.

5. The catheter assembly of claim 2, further comprising a kink imparted to the distal part of the elongate element, proximally of the rounded tip of the elongate element.

6. The catheter assembly of claim 5, wherein the kink is arranged distally of the curvilinearly shaped portion of the elongate element, the kink defining an angled distal portion, which is arranged at a predetermined, acute angle relative to an axis of that part of the elongate element arranged proximally of the kink.

7. A catheter assembly comprising:
    a handle having a proximal end and a distal end;
    an elongate element extending from the distal end of the handle, the elongate element comprising:
        a distal end;
        a distal part having a curvilinearly shaped portion; and
        a bend-enhancing region located proximally of the curvilinearly shaped portion;
    a sleeve being axially displaceable relative to the elongate element between an extended position in which the sleeve collapses the curvilinearly shaped portion of the elongate element into a substantially rectilinear configuration and exposes the bend-enhancing region proximally of the sleeve, and a retracted position in which the curvilinearly shaped portion of the elongate element adopts a curvilinear shape and the sleeve exposes the bend-enhancing region distally of the sleeve to facilitate steering of the curvilinearly shaped portion of the elongate element;
    an electrode sheath carried on the distal end of the handle with the elongate element being received within a lumen of the electrode sheath, the electrode sheath covering the distal end of the elongate element in the retracted position; and a control mechanism carried on the handle for effecting control of the axial displacement of the sleeve.

8. The catheter assembly of claim 7, wherein the control mechanism comprises a slider arrangement that is axially slidably arranged on the handle to facilitate displacement of the sleeve from the extended position to the retracted position and vice versa.

9. The catheter assembly of claim 7, wherein the electrode sheath has a distal end preformed into a predetermined shape.

10. The catheter assembly of claim 9, wherein the preformed distal end of the electrode sheath has a shape corresponding to, and imparted by, the curvilinearly shaped portion of the distal part of the elongate element.

\* \* \* \* \*

UNITED STATES PATENT AND TRADEMARK OFFICE
CERTIFICATE OF CORRECTION

| | | Page 1 of 1 |
|---|---|---|
| PATENT NO. | : 8,977,333 B2 | |
| APPLICATION NO. | : 12/299762 | |
| DATED | : March 10, 2015 | |
| INVENTOR(S) | : Neil L. Anderson et al. | |

It is certified that error appears in the above-identified patent and that said Letters Patent is hereby corrected as shown below:

In the specification:
    COLUMN 6,    LINE 64,    change "forming" to --deforming--

Signed and Sealed this
Twenty-second Day of December, 2015

Michelle K. Lee
*Director of the United States Patent and Trademark Office*